United States Patent [19]

Hillstead

[11] Patent Number: 5,071,411
[45] Date of Patent: Dec. 10, 1991

[54] PRESSURE-ACTUATED VALVE FOR SEALING FLOW CONDUIT

[75] Inventor: Richard A. Hillstead, Miramar, Fla.

[73] Assignee: Cordis Corporation, Miami Lakes, Fla.

[21] Appl. No.: 498,707

[22] Filed: Mar. 26, 1990

[51] Int. Cl.⁵ .................... A61M 5/00; A61M 25/00
[52] U.S. Cl. .......................... 604/246; 604/9; 604/264; 604/280; 251/5; 251/341; 251/343; 251/349
[58] Field of Search ............... 604/9, 158, 202, 205, 604/212, 213, 236, 245, 247, 249, 335, 905, 264, 280; 137/71, 844, 843, 860; 251/341, 343, 349, 4, 5

[56] References Cited

U.S. PATENT DOCUMENTS

| | | | |
|---|---|---|---|
| 2,941,544 | 6/1960 | Peras | 137/844 |
| 3,794,223 | 2/1974 | Patel | 604/249 |
| 3,965,925 | 6/1976 | Gooch | 251/4 |
| 4,000,739 | 1/1977 | Stevens | 604/167 |
| 4,092,010 | 5/1978 | Carlson, Jr. | 251/4 |
| 4,468,224 | 8/1984 | Enzmann et al. | 604/247 |
| 4,473,067 | 9/1984 | Schiff | 604/158 |
| 4,610,665 | 9/1986 | Matsumoto et al. | 604/167 |
| 4,626,245 | 12/1986 | Weinstein | 604/256 |
| 4,798,594 | 1/1989 | Hillstead | 604/167 |
| 4,895,346 | 1/1990 | Steigerwald | 604/247 |
| 4,895,565 | 1/1990 | Hillstead | 604/167 |
| 4,946,133 | 8/1990 | Johnson et al. | 137/844 |
| 4,950,254 | 8/1990 | Andersen et al. | 604/247 |

Primary Examiner—C. Fred Rosenbaum
Assistant Examiner—Chalin Smith
Attorney, Agent, or Firm—Gerstman & Ellis, Ltd.

[57] ABSTRACT

A pressure-actuated valve for sealing a flow conduit. The valve comprises a housing, and a tubular resilient valve carried within the housing. The tubular valve defines a lumen extending through the housing. Means are provided for varying the pressure in the space within the housing but outside of the tubular valve. Thus, the tubular valve can be urged to collapse inwardly by specific pressure applied.

19 Claims, 2 Drawing Sheets

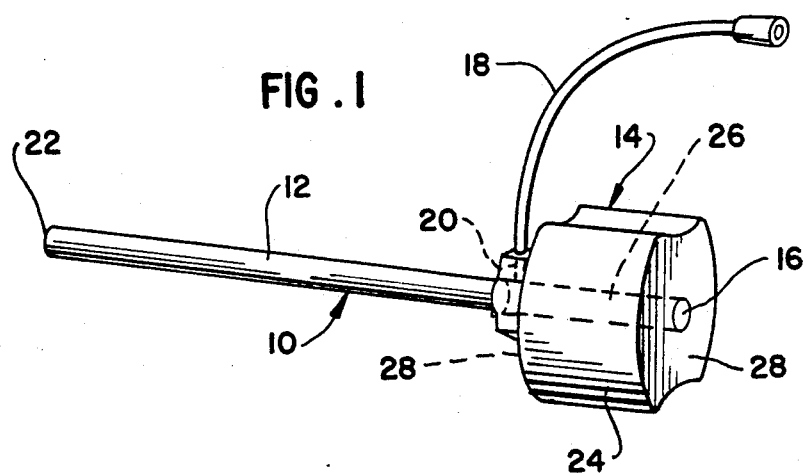
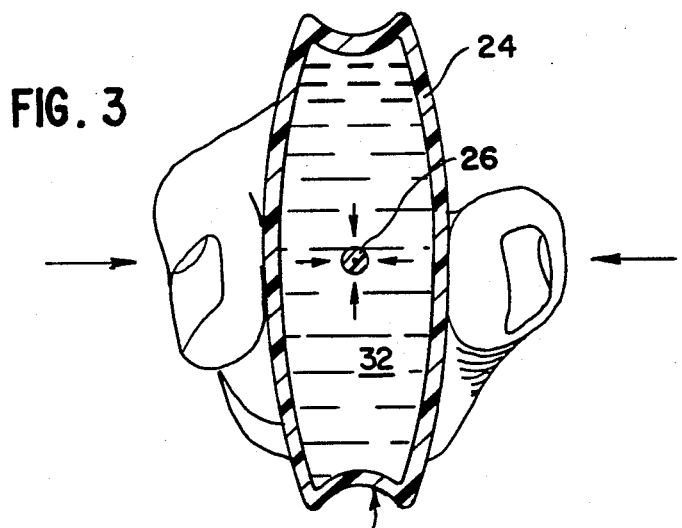
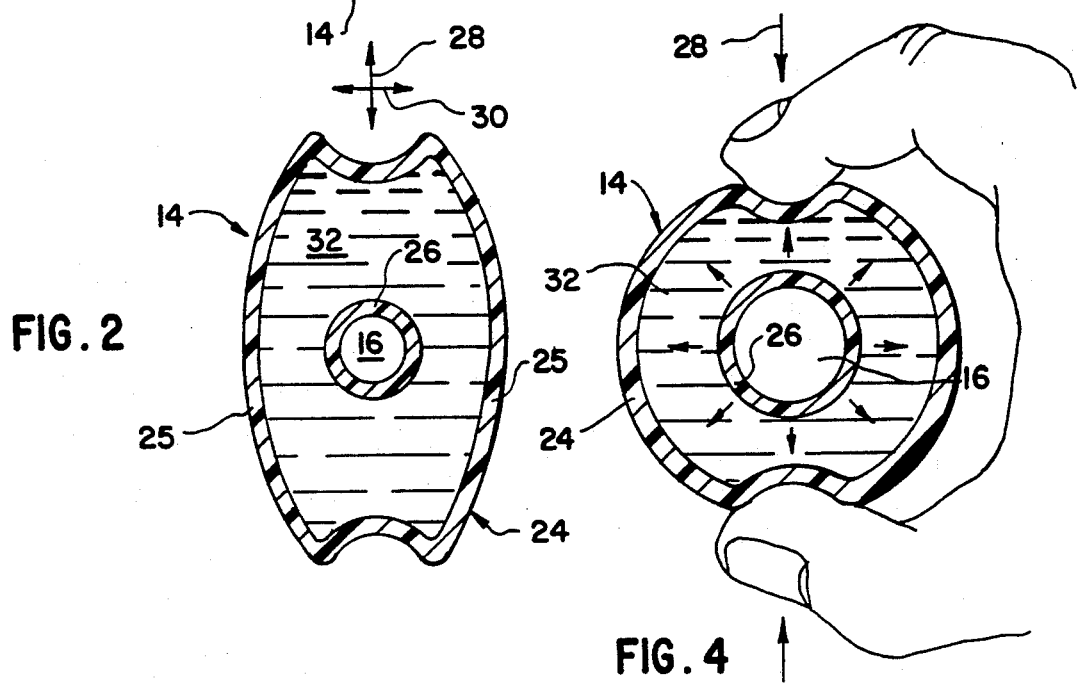

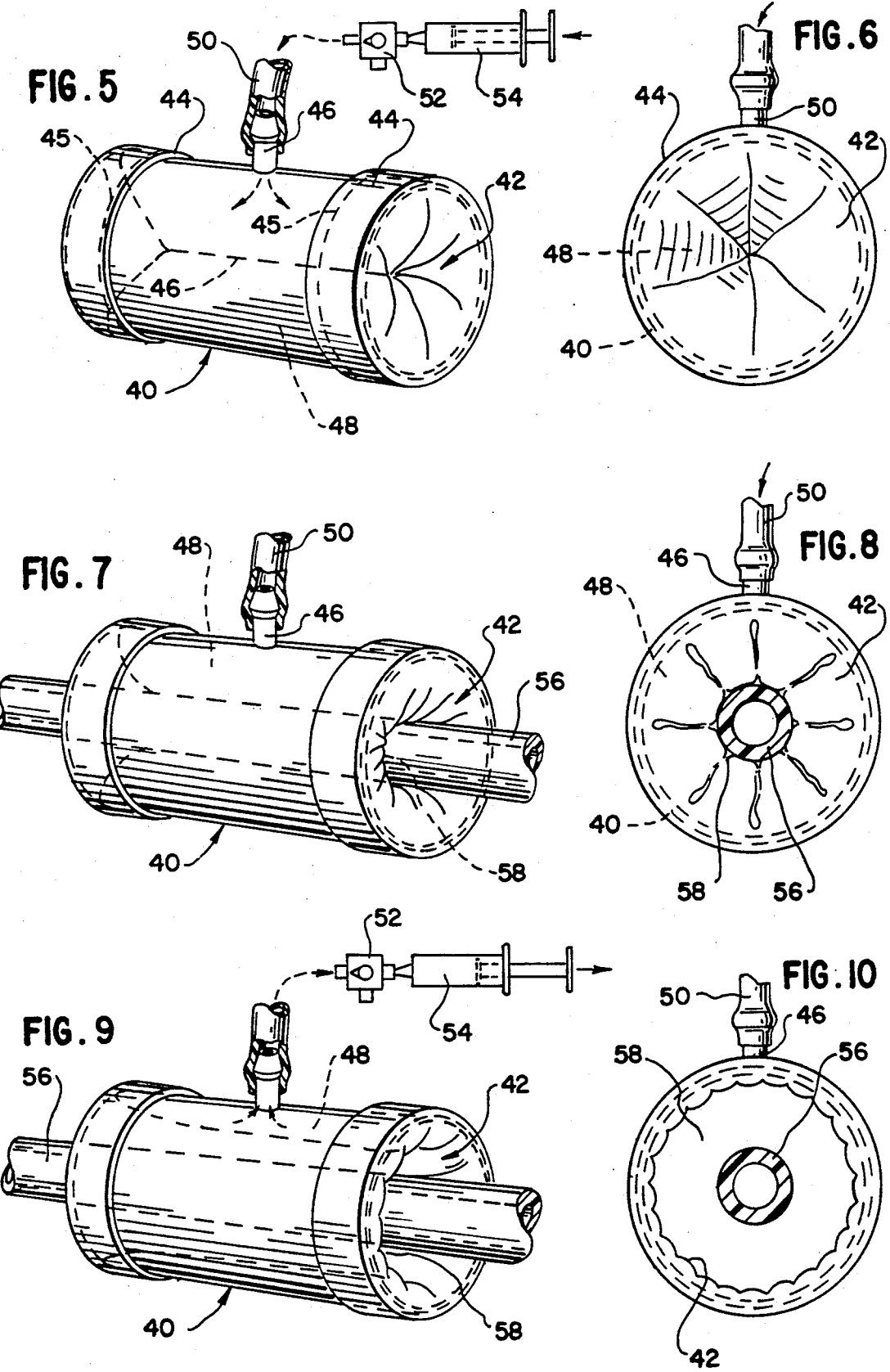

PRESSURE-ACTUATED VALVE FOR SEALING FLOW CONDUIT

BACKGROUND OF THE INVENTION

Hemostasis valves are well-known, being currently used for example in arterial catheter introducers, which are used with catheters for performing percutaneous transluminal coronary angioplasty (PTCA), as well as catheters for angiographic procedures, for example where x-ray contrast fluid is inserted through a catheter into the coronary artery. The hemostasis valve is typically used to prevent the leakage of blood out of or around dilatation and other catheters which particularly extend into an artery, to prevent the reverse seepage of blood out of the patient into the operating field. Typically, hemostasis valves are conventionally positioned at the proximal ends of catheter introducers, which are used to facilitate the entrance of catheters into an artery or other blood vessel.

Numerous types of hemostasis valves are known. By way of example, see Stevens U.S. Pat. No. 4,000,739, Matsumoto, et al. U.S. Pat. No. 4,610,655, Weinstein U.S. Pat. No. 4,626,245, and Hillstead U.S. Pat. No. 4,798,594.

While many of the commercially available hemostasis valves are fairly tolerant of various diameters of probes and catheters passing through them, to permit good sealing over a relatively large diameter range, all of the currently available valves have significant limitations as to the variation in catheter diameter which can pass through the valve without damaging it, and while providing good sealing.

In accordance with this invention, a valve is provided for elongated members such as probes and catheters in which the same valve can provide sealing against a greatly increased range of probe or catheter diameters. Additionally, while difficulties in passing a probe or catheter through prior valves have been noted, the valve of this invention, which may be pressure-actuated, can provide a wide aperture for insertion of a probe or catheter, and then can provide a sealing pressure against such probe or catheter of any desired amount, limited primarily by the strength of the materials involved. Also, the pressure-actuated valve of this invention may be positively closed for sealing at any desired pressure, to provide any desired level of sealing against high pressures when a catheter or probe is not penetrating therethrough.

Thus, the pressure-actuated valves of this invention exhibit great versatility and effectiveness, particularly in their preferred use as a hemostasis valve on a catheter sheath introducer or any other desired medical device. Additionally, the valve of this invention may be used in any other desired non-medical application.

DESCRIPTION OF THE INVENTION

In this invention, a pressure-actuated valve for sealing a flow conduit is provided. The valve comprises a housing, with a tubular, resilient valve member carried within the housing. The tubular valve member defines a lumen extending through the housing which is typically part of the flow conduit, which flow conduit passes through the lumen.

Means are provided for varying the pressure in the space within the housing that is outside of the tubular valve member. Thus, the tubular valve member can be urged to collapse inwardly by increased pressure in the space recited above, and it can also be urged to expand outwardly by decreased pressure in the space, depending on the specific pressure applied. Of course, the valve of this invention can also be operated at ambient pressures, when no specific pressure is applied to the space within the housing but outside of the tubular valve member.

In one embodiment, the housing may define a flexible, outer wall enclosing a sealed volume outside of the tubular valve member. In this case it may be preferred for one transverse dimension of the housing to ba greater than a perpendicular transverse dimension thereof. For example, the one transverse dimension may be at least one third greater than the perpendicular transverse dimension. In such a circumstance, transverse compression of the housing along the one dimension can urge the tubular valve member to expand outwardly. Contrariwise, transverse compression of the housing along the perpendicular, shorter transverse dimension can urge the tubular valve member to collapse inwardly.

While this result may be surprising at first consideration, there is an understood reason for it. While applicant does not wish to be bound by any theoretical considerations, it is believed that when a flexible-walled housing of relatively fixed volume has one transverse dimension that is longer than its other perpendicular transverse dimension, and one collapses the housing along the larger transverse dimension, the cross sectional area of the housing actually increases. This can be illustrated by a rectangle having respective opposite sides of one and three inches. Its area is of course three square inches. However, if one squeezes the rectangle so that it becomes a square having sides of two inches, its peripheral length remains the same, but its area increases to four square inches. Thus, an overall enlargement of the volume of the housing can take place by squeezing the longer transverse dimension of the tubular valve member of this invention. Such an increase in volume results in a reduction of pressure, which urges the tubular valve member to expand.

To the contrary, when one squeezes the housing along its shorter, perpendicular transverse dimension, one is making the cross sectional area of the area thinner and flatter, with a reduction of the cross sectional area and a consequent reduction of volume. Thus, the internal pressure is increased, urging the tubular valve member to collapse inwardly.

It is generally preferred for the sealed volume to be filled with an incompressible fluid, and for the tubular, resilient valve member to be more resilient than the flexible, outer wall. For example, the tubular, resilient valve member may be made of a true elastomer such as natural rubber latex or silicone rubber. The flexible, outer wall may ba made of a tough but flexible plastic such as poly(ethylene terephthalate), nylon, polyethylene, or the like, which can be flexible but relatively inelastic.

In another embodiment of the valve of this invention, the housing, which is typically relatively rigid, but which may be semi-flexible, also defines a wall enclosing a sealed volume outside of the tubular valve member which is carried by the housing. A pressure port communicates between the sealed volume and the exterior, to permit fluid pressure control in the sealed volume. Thus, by the control of the pressure in the sealed volume through the pressure port, one can urge the tubular valve member to collapse inwardly, or alternatively to expand outwardly, as may be desired. Of course, the third alternative is to use the valve without pressure control when that is desired.

In this latter embodiment the pressure port may communicate typically through a flexible tube with valve means for alternative sealing of, or opening for pressure control through, the pressure port. Thus, a given pressure may be applied through the open valve means to the sealed volume, and then the valve may be closed so that the desired pressure is maintained in the sealed volume. Thus, the valve exhibits certain sealing characteristics at this pressure. Then, if desired, the valve may be opened again to vent the system, or to change the pressure from positive to reduced, relative to atmospheric pressure. Then the port may be resealed by the valve means again if desired.

Typically, pressure application means may be provided to communicate with the valve means. For example, a conventional syringe may be used to provide either positive or reduced pressures through the valve into the sealed volume. Otherwise, a squeeze bulb may be permanently attached to the valve, if desired, for providing desired, particularly positive, pressures to the sealed volume.

Thus, a versatile, adjustable, and reliable valve may be provided for sealing a flow conduit, being particularly desirable for use as a hemostasis valve in conjunction with medical apparatus such as a catheter introducer.

DESCRIPTION OF THE DRAWINGS

In the drawings, FIG. 1 is a perspective view of a catheter introducer which carries one embodiment of the pressure-actuated valve of this invention.

FIGS. 2 through 4 are enlarged, transverse sectional views of the pressure-actuated valve of FIG. 1, showing how it may be manually manipulated.

FIG. 5 is a perspective view of another embodiment of the pressure-actuated valve of this invention, shown in pressurized form without an elongated member penetrating through it.

FIG. 6 is an end elevational view of the valve of FIG. 5.

FIG. 7 is a perspective view of the pressure-actuated valve of FIG. 5, shown in pressurized condition with a catheter extending through it.

FIG. 8 is an end elevational view, taken partly in section, of FIG. 7.

FIG. 9 is a perspective view of the pressure-actuated valve of FIG. 7 with a catheter penetrating through it, showing the valve in a reduced pressure mode.

FIG. 10 is an end elevational view, taken partly in section, of FIG. 9.

DESCRIPTION OF SPECIFIC EMBODIMENTS

Referring to FIGS. 1 through 4, a catheter introducer 10 is shown which may be of conventional design except for the modifications provided by this invention.

Catheter introducer 10 defines a plastic sheath 12 which is carried at the distal end of housing 14. Sheath 12 forms an extension of lumen 16 which is defined through housing 14. Also, as is conventional, a side tube 18 communicates through port 20 with lumen 16 of housing 14.

As is well known, a catheter sheath introducer may be used to facilitate the entry of arterial catheters into and out of an artery. The distal end 22 of sheath 12 penetrates the artery wall by means of a known surgical technique. Then, a catheter can penetrate lumen 16 and the bore of sheath 12 to enter the artery, without causing undesirable abrasion of the tissue of the artery access site.

Housing 14 defies the pressure-actuated valve of this invention for sealing the flow conduit defined by lumen 16 and the bore of sheath 12. In this particular embodiment, housing 14 defines a flexible outer wall 24 which may be made of PET or another plastic which is flexible but preferably with relatively low resilience. As shown in FIGS. 2-4, the outer wall 24 of housing 14 encloses a tubular, resilient valve member 26 which may be sealed in any desirable manner to the end walls 28 of housing 14, and which may be made of preferably an elastomer such as natural rubber latex, to be substantially more resilient than the outer wall 24 of housing 14.

Thus, flexible outer wall 24, in conjunction with end walls 28, defines a sealed volume 32 outside of tubular valve member 26, as generally shown in FIGS. 2-4. If the material of outer wall 24, including end walls 28, is relatively non-resilient, the sealed volume is relatively constant at variable pressures.

FIG. 2 shows the normal cross sectional configuration of housing 14 in its natural, unstressed condition. In that condition, lumen 16 is of a predetermined size, being defined through tubular, resilient valve member 26. In this circumstance, it is possible to insert a catheter or other probe through lumen 16 and the bore of sheath 12 to enter the arterial system. However, leakage of blood may occur between the inner wall of tubular valve 26 and the catheter or other probe being inserted through lumen 16. Alternatively, the inner diameter of tubular valve 26 in its natural, unstressed configuration may be too small for the convenient insertion of a desired catheter or other probe. In accordance with this invention, the inner diameter of lumen 16 may be adjusted by pressure actuation to either provide improved sealing, or to expand the inner diameter to facilitate the insertion or withdrawal of a catheter or the like.

As shown in FIG. 2, housing 14 in its natural, unstressed condition defines one transverse dimension 28 which is greater than a perpendicular transverse dimension 30 of the housing. The longer transverse dimension 28 of the cross sectional view of FIG. 2 is shown to be approximately 50 per cent greater than the shorter transverse dimension 30, measuring in each case the maximum transverse dimension of the sealed volume 32 within housing wall 24.

Because of this difference in the two transverse dimensions, the sealed volume 32 in the natural, unstressed configuration of housing 14, can be in a roughly oval or elongated rectangular configuration, although it is understood that the cross sectional, inner configuration of the housing of this invention does not have to be either oval or elongated rectangular in shape, but may be of essentially any desired cross sectional shape in which preferably one transverse dimension is greater than the other.

It is also preferred for the sealed volume 32 to be filled with an incompressible fluid such as water, or a relatively viscous gel such as silicone gel, mineral oil gel or the like. However, it is also possible for sealed volume 32 to be filled with air or another gas.

Accordingly, when one squeezes housing 14 along the shorter transverse dimension 30, the cross sectional shape of housing 14 tends to become longer and thinner, as can be seen by comparison between the unstressed configuration of FIG. 2 and the configuration of FIG. 3. As is well known from simple geometry, a geometric figure of the same periphery as another geometric figure but which is longer and flatter, tends to have less area. Thus, the squeezing of housing 14 along transverse dimension 30 causes its volume to reduce to the degree that there is no corresponding stretching in housing wall 24. This increases the pressure within sealed volume 32, which causes the collapsing of tubular, resilient valve 26, as shown. Thus, it becomes possible to collapse lumen 16 to form a seal by the simple application of transverse pressure along dimension 30, either with the fingers for momentary sealing, or with a clamp, if desired, for longer term but releasable sealing. If a catheter or other probe is carried within lumen 16 when one compresses housing 14 along dimension 30, tubular valve 26 will collapse about the catheter to provide a seal between the inner wall of tubular valve 26 and the catheter surface. Thus, it becomes possible to provide any level of sealing desired, dependent upon the pressure applied to housing 14 along transverse dimension 30, either manually or with a clamp, to particularly prevent the leakage of blood proximally out of catheter introducer 10, either with or without a catheter present.

Contrariwise, as shown in FIG. 4, it may be desired to insert a catheter which has an outer diameter equal to or greater than the normal diameter of lumen 16 in the unstressed condition of FIG. 2. The pressure-actuated valve of FIGS. 1-4 is capable of expansion as well as contraction, so that a catheter or other probe may be inserted into an expanded lumen for easy installation without frictional difficulties. Then, the lumen may be contracted again to provide a spontaneous seal against the catheter. If desired, additional sealing may be provided by the exertion of pressure in the direction of transverse dimension 30.

The expansion of lumen 16 is accomplished as shown in FIG. 4 by compression of housing 14 in the direction of the one transverse dimension 28. Such pressure of course causes flexible housing wall 24 to collapse in dimension 28, causing the transverse dimensions of housing 14 to become more equal. When two geometric figures such as rectangle or oval are of equal peripheral length, the geometric figure having perpendicular axes which are closer to equal will have the greater area. Thus, the shape to which housing 14 has been pressed in FIG. 4 exhibits a greater area than the corresponding cross sectional area of FIG. 2, with the result that the volume of housing 14 tends to increase as it is squeezed to the configuration of FIG. 4. This effect shows up particularly well when sealed volume 32 is filled with an incompressible fluid, and the material of wall 24 is stiff enough to prevent its inward bowing. Also, the outwardly curved, major surfaces 25 of wall 24 help to resist inward bowing. Thus, upon the squeezing as shown in FIG. 4, a reduced pressure is created in sealed volume 32, which causes the outward stretching and expansion of tubular, resilient valve 26 and the enlargement of lumen 16.

The configuration of FIG. 4 is typically provided for only a relatively brief moment, to facilitate the insertion of a catheter or the like. Then, housing 14 can be released, and it tends to snap back to the configuration of FIG. 2, with tubular valve 26 shrinking as far as it can to provide a natural pressure seal about the catheter or other probe that passes through it.

Thus, in accordance with this invention, it is possible to insert oversized catheters through the pressure-actuated valve of this invention, and then to release the valve to cause tubular valve member 26 to shrink back with a pressure seal about the catheter, if the catheter has a larger diameter than the normal diameter of lumen 16. As was stated before, added pressure sealing may be provided by further pressurization of housing 14 along transverse dimension 30. Likewise, undersized catheters, probes and the like may be inserted through the pressure-actuated valve of this invention by inserting the catheter which loosely fits in lumen 16, and then applying transverse pressure to housing 14 along dimension 30, to prevent leaking about the installed catheter.

Accordingly, the valve of this invention exhibits great flexibility with respect to the diameter of the probes that may be passed through the valve, while exhibiting good capability for any degree of sealing which may be desired around any catheter or probe passing through the valve, or when no catheter or probe is present.

Referring to FIGS. 5-10, another embodiment of the pressure-actuated valve of this invention is disclosed. In this embodiment, housing 40 defines a wall which encloses a sealed volume outside of a tubular valve member 42. In this embodiment, housing 40 is preferably rigid, or possibly semiflexible, while tubular valve member 42 is, once again, an elastomeric tube of latex, silicone rubber, or the like. As shown in FIG. 5, housing 40 is of tubular shape, while tubular valve member 42 fits within the housing, extending therethrough with the ends 44 of tubular valve member 42 being convoluted outwardly and sealed with an annular seal 45 to respective outer surfaces of the ends of housing 40.

Housing 40 also defines a pressure port 46 for communicating with a sealed volume 48, which is the volume inside of housing 40 but outside of tubular valve 42. Pressure port 46 communicates between sealed volume 48 and the exterior to permit fluid pressure control in the sealed volume. Specifically port 46 is attached to flexible tubing 50 which, in turn, communicates with a conventional three-way valve 52. Valve 52 permits communication between port 56 and a pressure applying means such as syringe 54 in one position, but also closes off communication so that sealed volume 48 may be closed off and the desired pressure maintained. Additionally, three way valve 52 may have a venting position if desired so that positive or reduced pressures within sealed volume 48 may be vented to atmospheric pressure when desired.

In the configuration of FIGS. 5 and 6, sealed volume 48 is pressurized, so that resilient tubular valve 42 expands inwardly to close the lumen normally defined by valve 42 to form a seal line 46, thus closing off any flow path through housing 40. Normally, housing 40 may be mounted in a catheter introducer, or carried on a catheter or other device which defines a flow path which is to be provided with valving action by the pressure-actuated valve of this invention.

Specifically, the configuration of FIG. 5 can be achieved by opening three way valve 52, and applying compressed air by means of syringe 54 through port 46 into sealed volume 48 until the formerly present lumen in tubular, resilient valve 42 is closed and sealed. When it is desired to open the valve again, one can simply cause three way valve 52 to vent, resulting in the recreation of a lumen through tubular valve member 42.

Referring to FIGS. 7 and 8, the same valve having housing 40, and tubular resilient valve member 42, is opened to define a lumen 58, for example by an application of reduced or suction pressure by syringe 54 through port 46. Then a catheter 56 or other probe may be inserted into the lumen 58 that is normally defined by tubular, resilient valve member 42. Following this, as desired, one may provide an increased pressure to sealed volume 48 through port 46 by means of syringe 54 and three way valve 52, followed by typically closing valve 52 so that the increased pressure remains in sealed volume 48. Thus, tubular valve member 42 firmly presses against catheter 56 to provide the desired seal. When and if it is desired to move catheter 56 longitudinally with respect to housing 40, one may release the pressure by proper adjustment of three way valve 52, or one may increase it by use of syringe 54, as may be desired to provide exactly the right pressure, moment by moment, to permit the easy movement of catheter 56 through the valve while minimizing or eliminating any leakage of blood or the like between catheter 56 and tubular valve 42.

Particularly as shown in FIGS. 9 and 10, the same valve including housing 40 may be subjected to a larger suction pressure within sealed volume 48, so that the lumen 58 of tubular valve member 42 is expanded to provide a space around catheter 56. Thus, it can be seen that catheter 56 may be easily advanced without frictional considerations. Then, when it as desired, tubular, resilient valve member 42 may be collapsed again by repressurization, with syringe 54, of sealed volume 48 which is inside of housing 40 and outside of tubular valve member 42.

If desired, syringe 54 may be replaced with any other desired pressure applying device including a source of pressurized fluid, gas or liquid from a master supply, or a squeeze bulb.

Thus, by appropriate manipulation of three way valve 52 and syringe 54 or its equivalent, the pressure-actuated valve of this invention can exert any desired level of sealing pressure against itself to seal the empty valve, or to seal around a catheter or other probe which is passing through the valve, in a manner which is adjustable. This permits longitudinal movement of the catheter, or hard, relatively high pressure sealing, as may be desired.

The above has been offered for illustrative purposes only, and is not intended to limit the scope of the invention of this application, which is as defined in the claims below.

That which is claimed is:

1. A pressure-actuated valve for sealing a flow conduit, which comprises:
   a housing defining a pressurizable interior; a tubular, resilient valve member carried within said housing, said tubular valve member defining a lumen extending through said housing, said housing defining a fluid-filled space outside of said tubular valve member; and means for varying the fluid pressure in the space within said housing outside of said tubular valve member, whereby said tubular valve member can be urged to collapse inwardly by specific fluid pressure applied.

2. The valve of claim 1 in which said housing defines a flexible, outer wall enclosing a sealed volume outside of said tubular valve member.

3. The valve of claim 2 in which one transverse dimension of said housing is greater than a perpendicular transverse dimension thereof, whereby transverse compression of said housing along said one transverse dimension can urge said tubular valve member to expand outwardly, while transverse compression of said housing along the perpendicular transverse dimension can urge the tubular valve to collapse inwardly.

4. The valve of claim 3 in which said one transverse dimension is at least one third greater than said perpendicular transverse dimension.

5. The valve of claim 3 in which at least some of the portions of said outer wall extending generally in said one transverse dimension are outwardly curved.

6. The valve of claim 2 in which said sealed volume is filled with an incompressible fluid.

7. The valve of claim 2 in which said tubular, resilient valve member is more resilient than said flexible, outer wall.

8. The valve of claim 1 in which said housing defines a wall enclosing a sealed volume outside of said tubular valve member, and a pressure port communicating between said sealed volume and the exterior to permit fluid pressure control in said sealed volume, to urge said tubular valve member to collapse inwardly or expand outwardly as desired.

9. The valve of claim 8 in which said pressure port communicates with valve means for alternative sealing of, or opening for pressure control of, said pressure port.

10. The valve of claim 9 having pressure application means communicating with said valve means.

11. A catheter introducer which carries at a proximal end thereof the valve of claim 1.

12. A pressure-actuated valve for sealing a flow conduit, which comprises:
    a housing; a tubular, resilient valve member carried within said housing; said tubular valve member defining a lumen extending through said housing; in which said housing defines a flexible, outer wall enclosing a sealed volume outside of said tubular valve member, said tubular valve member being more resilient than said flexible, outer wall and in which one transverse dimension of the housing is greater than a perpendicular transverse dimension thereof, whereby transverse pressure of the housing along said one transverse dimension can urge said tubular valve member to expand outwardly, and transverse compression of the housing along the transverse dimension perpendicular to said one transverse dimension can urge said tubular valve to collapse inwardly.

13. The valve of claim 12 in which at least some of the portions of said outer wall extending generally in said one transverse dimension are outwardly curved.

14. The valve of claim 12 in which said sealed volume is filled with an incompressible fluid.

15. The valve of claim 12 in which said one transverse dimension is at least one third greater than said perpendicular transverse dimension.

16. A catheter introducer which carries at a proximal end thereof the valve of claim 12.

17. A catheter introducer which defines a sheath having a bore for receiving a catheter, said sheath defining a proximal end which carries a pressure-actuated valve for sealing the bore through the sheath, said pressure-actuated valve defining a housing; a tubular, resilient valve member carried within said housing, said tubular valve member defining a lumen extending through said housing; said housing defining a wall enclosing sealed volume outside of said tubular valve member and a pressure port communicating between said sealed volume and the exterior to permit fluid pressure control in said sealed volume, to urge said tubular valve member to collapse inwardly or expand outwardly as desired; said pressure port communicating with valve means for alternative sealing of, or opening for pressure control of, said pressure port, and pressure application means communicating with said valve means.

18. The catheter introducer of claim 17 in which said pressure application means is a syringe.

19. The catheter introducer means of claim 17 in which said housing is tubular in shape and said tubular, resilient valve member extends through said housing and reversely convolutes outwardly at both ends, being sealed with an annular seal to opposed outer ends of said tubular housing.

* * * * *